United States Patent [19]

Welker

[11] 4,403,519
[45] Sep. 13, 1983

[54] SAMPLE COLLECTION APPARATUS

[75] Inventor: Robert H. Welker, Sugar Land, Tex.

[73] Assignee: Welker Engineering Company, Sugar Land, Tex.

[21] Appl. No.: 280,658

[22] Filed: Jul. 6, 1981

[51] Int. Cl.³ ............................ G01N 1/10; B01F 7/26
[52] U.S. Cl. .............................. 73/864.62; 73/864.91; 366/332; 74/512
[58] Field of Search ................... 73/864.62, 864.91; 366/332, 333, 256, 289, 315; 74/512, 560; 417/903

[56] References Cited

U.S. PATENT DOCUMENTS

| | | | |
|---|---|---|---|
| 918,508 | 4/1909 | Colman | 366/332 |
| 1,228,934 | 6/1917 | Leo | 74/512 |
| 2,204,867 | 6/1940 | Rehback | 74/512 |
| 2,770,364 | 11/1956 | Honea | 366/289 X |
| 2,831,606 | 4/1958 | Alters | 366/332 X |
| 2,942,296 | 6/1960 | Hewatt | 74/512 X |
| 3,368,697 | 2/1968 | Carlson | 188/312 X |
| 3,793,888 | 2/1974 | Rosenwald | 73/864.62 |
| 4,172,670 | 10/1979 | Welker | 366/332 |
| 4,286,515 | 9/1981 | Baumann | 100/233 |

Primary Examiner—Charles A. Ruehl
Assistant Examiner—John E. Chapman, Jr.
Attorney, Agent, or Firm—Gunn, Lee & Jackson

[57] ABSTRACT

Sample collection apparatus is disclosed wherein the preferred and illustrated embodiment includes a cylinder enclosing a piston which defines a storage chamber below the piston. The storage chamber is provided with an inlet in a cylinder head at the lower end of the cylinder. The storage chamber is maintained under pressure by pressurizing the opposite side of the piston. A stirring disc is located in the storage chamber. The stirring disc is in the form of a plate, and it is agitated by a rod connected to it. This stirs the sample to prevent separation into strata of different ingredients. The rod connected to the stirring disc passes through the head at one end of the cylinder and extends from it. In one embodiment, the rod is attached to a small piston which is pressurized in a cylinder to be driven in one direction or the other to stir the sample. In another embodiment, the rod extends downwardly in a surrounding tubular wall and is aligned therewith, and supports a foot operated treadle which can be pumped by the user to stir the sample.

5 Claims, 3 Drawing Figures

SAMPLE COLLECTION APPARATUS

BACKGROUND OF THE DISCLOSURE

The present inventor devised U.S. Pat. No. 4,172,670 as a sample collection apparatus. That structure has functioned quite well. It is particularly valuable in collection of small samples, typically in the range of one or two liters. When the sample must be larger, perhaps five or ten liters, the apparatus becomes somewhat tall, perhaps objectionably so. As will be appreciated, scaling the structure up is no problem in terms of manufacture but it is sometimes a problem in installation. It is generally undesirable to have an apparatus which stands taller than about eight feet because it is difficult to install under low ceilings. Moreover, some hand strength is required to grip the handle and stir the accumulated sample. In light of the scale limitations which are noted above, it has been determined that an alternate sample collection apparatus be provided. This structure, actually having the form of alternate embodiments, overcomes the difficulties mentioned above. First of all, it provides a structure which is substantially shorter. It is not merely a matter of changing the scale so that the storage chamber is greater in diameter; as the diameter of the stirring disc increases, the strength required to reciprocate it likewise increases. It is very easy to stir a small diameter sample container while it requires more strength to do this with a larger diameter disc. Accordingly, to provide a five or ten liter sample collection apparatus, this disclosure sets forth a shorter collection apparatus which will fit beneath a low ceiling so that structural or building modifications are not required for its installation. It also provides a means whereby the stirring disc in the sample collection chamber can be reciprocated.

On the latter point, this disclosure sets forth alternate means. The first is obtained through the use of a double acting piston appended to the sample collection apparatus. The piston is received within the chamber and is acted on by pressure fluid on both faces thereby yielding a double acting arrangement. The piston in turn is connected to a rod which joins to the stirring disc. In the other embodiment, foot power of the operator is used. The rod which extends from the stirring disc downwardly is centralized within a hollow upstanding pipe which has a window cut in one side. The rod connects to a stirrup which can be foot actuated. A window is cut to enable the user to insert his foot into the stirrup to force the stirring disc upwardly and downwardly. This permits the user to stir manually through the use of his body weight as opposed to hand stirring.

Moreover, this structure is also relatively short so that it can fit beneath conventional ceiling heights.

Through the use of the structure disclosed herein, large samples can be collected. Even should the sample stratify in the sample collection chamber, it can be stirred with a great deal of turbulence to adequately mix the sample.

BRIEF DESCRIPTION OF THE APPARATUS

This apparatus discloses a cylinder surrounding a piston. The piston is enclosed between facing cylinder heads. The lower side of the piston defines a sample storage chamber. The upper side defines a pressurization chamber to provide adequate back pressure bearing against the sample. The back pressure forces the piston against the sample so that the sample is maintained in a liquid state to avoid partial vaporization of the sample. Moreover, the piston is steadily forced upwardly against back pressure as the sample accumulates. As the piston is moved upwardly with increases in sample size, the sample is eventually accumulated to capacity of the storage device. At this juncture, it is desirable to remove the sample.

The device of this disclosure stirs the sample through reciprocation of a stirring disc in the sample receiving chamber. This disc extends transversely of the cylindrical storage chamber, and flushes the accumulated sample about the edges with turbulence to commingle the sample and break up strata in the sample. The stirring disc is mounted on a rod which reciprocates. Alternate embodiments are disclosed wherein the sample stirring rod is either powered by a hydraulic cylinder which is bidirectionally powered or in the alternative, it is powered by a foot operated stirrup.

BRIEF DESCRIPTION OF THE DRAWINGS

So that the manner in which the above recited features, advantages and objects of the invention, as well as others, which will become apparent, are attained and can be understood in detail, a more particular description of the invention, briefly summarized above, may be had by reference to the embodiments thereof illustrated in the appended drawings, which drawings form a part of this specification. It is to be noted, however, that the appended drawings illustrate only typical embodiments of the invention and are not to be considered limiting of its scope, for the invention may admit to other equally effective embodiments.

DETAILED DESCRIPTION OF PREFERRED AND ILLUSTRATED EMBODIMENTS

Figure 1:
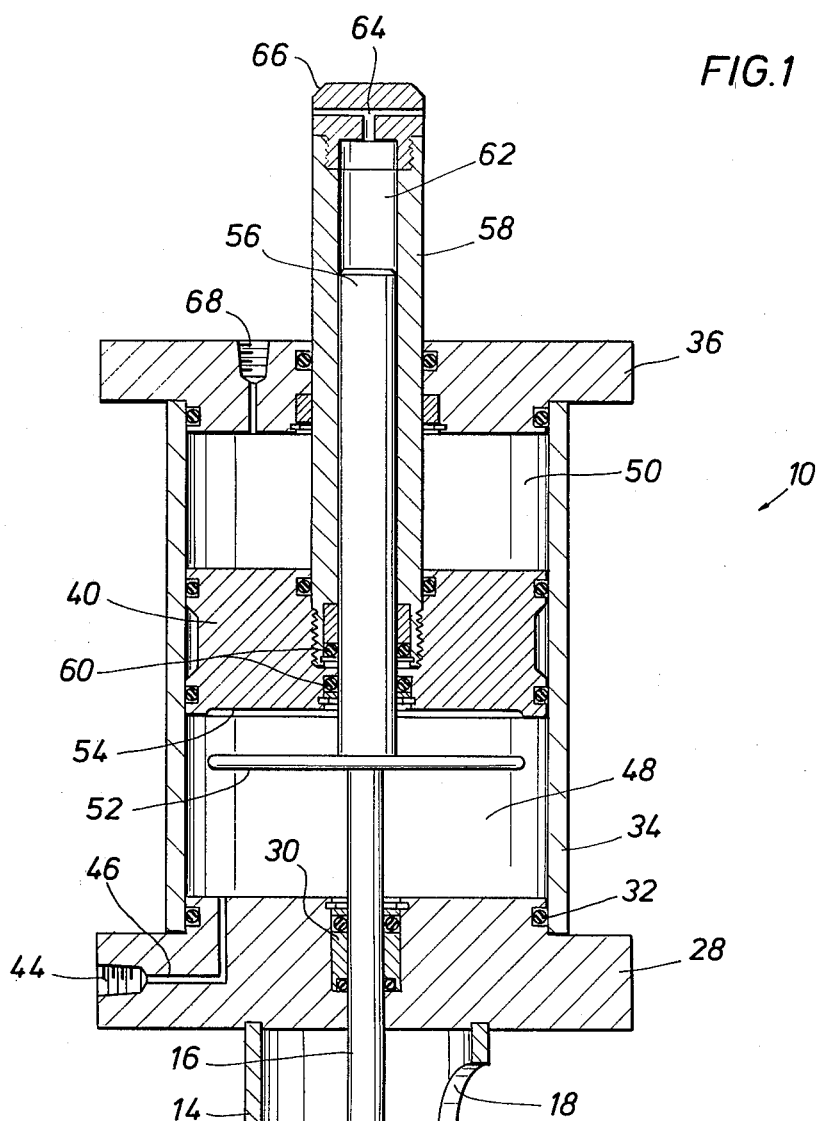
FIG. 1 is a sectional view through the sample storage apparatus of the present disclosure illustrating a foot operated stirrup connected to a stirring disc in the sample storage chamber.

Attention is first directed to FIG. 1 of the drawings where the sample storage apparatus is identified generally by the numeral 10. It will be described preceding from the base upwardly. It is shown supported on a base plate 12 which enables the equipment to be stationed at a convenient location standing in the upright position. The base plate is joined to and supports an upstanding cylindrical cage 14. A stirring rod 16 is concentric with the cage. The cage has a window cut at 18, and the window is elongate. The window has a width to receive a user's foot. The length of the window is sufficient to enable reciprocating strokes of the user's foot in an upward and downward motion. Moreover, the window extends substantially to the floor and has a height which is sufficient to prevent barking the shin of the user.

The stirring rod 16 is attached to a spider 20 at its lower end by welding or other suitable means. The spider extends outwardly to inverted U-shaped clevises 22 which are affixed to a plate 24. The plate 24 is generally horizontal so the user can place his foot on it in order to reciprocate the stirrup.

Figure 2:
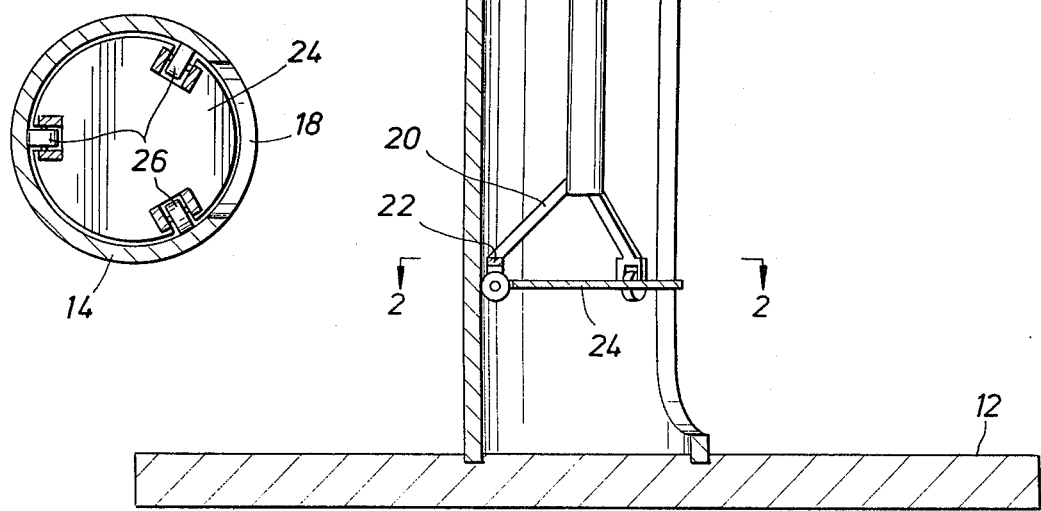
FIG. 2 is a sectional view along the line 2—2 of FIG. 1 showing details of construction of the foot powered stirrup.

The plate 24 is guided with the surrounding structure by means of rollers 26 which are mounted on suitable shafts. Ideally, three are used and they are spaced at 120 degree intervals around the plate. The window 18 is slightly less than 120 degrees in width. This enables the user to insert his foot between a pair of the rollers underneath the spider. The spider thus defines a position sufficiently large for the user to insert his foot onto the plate to force the stirrup downwardly. The plate is guided in upward and downward movement by the rollers 26. Needless to say, the rollers can be varied from the uniform spacing depicted in FIG. 2.

The stirrup is foot operated to force the stirring rod 16 downwardly. The rod 16 extends upwardly concentric of the cylindrical apparatus and passes through a lower cylinder head 28. The head 28 includes a seal mechanism at 30. This seals around the stirring rod 16. Moreover, the cylinder head 28 includes an upstanding circular lip and seal at 32 on the interior of a cylindrical wall 34. The cylinder 34 extends from the lower cylinder head 28 to an upper cylinder head 36. The cylinder heads are spaced from one another and are similarly constructed. Both are equipped with internal seals to define closed chambers within the cylinder 34, and they define the limits of travel of a piston 40. The piston 40 reciprocates within the cylinder 34 and leakage past the piston is prevented by seal rings. Moreover, the lower head 28 is drilled with a tapped hole at 44, and a passage 46 extends through the cylinder head into a lower chamber. The chamber beneath the piston 40 is identified by the numeral 48 while the top chamber is identified by 50. The two chambers are between the cylinder heads 28 and 36 on the interior of the cylindrical wall 34.

FIG. 1 further discloses a stirring disc or plate 52. It is joined to the stirring rod 16. Moreover, it is shaped to be received within a facial recess 54 on the lower side of the piston 40. It is also joined to and aligned with an upstanding rod 56. The rod 56 extends fully through the piston 40. The rod telescopes into a hollow sliding sleeve 58. The sleeve 58 is joined to the piston 40 by threads, and leakage along the rod 56 is prevented by the incorporation of suitable seals at 60. The seals 60 prevent leakage of the sample under pressure along the rod 56.

The rod 56 telescopes on the interior of a surrounding sleeve 58. The sleeve receives air at atmospheric pressure into a chamber 62, there being a small passage 64 in cap 66 for pressure relief. The sleeve 58 is closed over by a threaded cap 66 which is shown at the top of FIG. 1. The cap closes the sleeve to define the chamber 62. This chamber enables the rod 56 to telescope upwardly so that the stirring disc 52 may be retracted into the facial recess 54. When it is against the piston, it is completely retracted so that the chamber 48 is not divided by the stirring disc.

The stirring disc 52 has an expanse which covers a substantial portion of the cross-sectional area of the storage chamber 48. The clearance between the outer lip of the stirring disc and the adjacent cylindrical wall is relatively small. This enables the equipment to stir, churn or otherwise agitate the specimen stored in the chamber 48.

The pressure levels of the system should be noted. First of all, the top cylinder head 36 includes a tapped port 68 which admits hydraulic fluid under pressure. Preferably, the pressure that is maintained is a controlled back pressure. It fills the chamber 50 and forces the piston 40 downwardly. As sample is accumulated in the chamber 48, the sample is collected and forces the piston upwardly against back pressure in the chamber 50. Assume for instance that the sample is collected from a pipeline where the pressure is maintained at 1,000 psi. In these circumstances, the chamber 50 might be maintained at an intermediate pressure of perhaps 900 psi. This is sufficient to force the piston down before sample is accumulated. The sample is admitted at a controlled rate dependent on the sample size and duration. Sample is admitted at a rate which may require weeks or months to fill the chamber 48. In this interval, the ambient temperature may significantly drop, thereby reducing the temperature of the sample. Temperature reduction and stagnation typically lead to stratification of the sample. As the sample accumulates, the piston is forced upwardly. When the sample chamber is full, the piston is at the top-most extreme of travel. Moreover, the piston moves to this position when full capacity is achieved.

The two rods connected to the stirring disc 52 should be noted. The stirring rod 16 is of relatively small diameter while the rod 56 is larger. They are both exposed to the high pressure found in the chamber 48. Just as important, the ends of the rods are exposed to atmospheric pressure because they are protected by seals. There is an area differential between the two, and the high pressure in the chamber 48 forces the disc 52 upwardly into the recess provided for it. The high pressure creates a force proportional to the differential area. This force secures the disc in the recessed position during sample collection.

After the sample has been collected, and the chamber 48 has been filled, the sample can be selectively churned and mixed. The operator simply inserts his foot through the window 18 and places his foot on the plate 24 and pumps the stirrups downwardly. After the disc 52 is pumped down it will be forced back to the top by the pressure acting on the area differential as mentioned above. There is some displacement when the disc travels downwardly, this displacement of fluid being equal to the displacement achieved by sliding the larger rod 56 into the chamber 48. As this occurs, the chamber 48 must expand slightly. To this end, the piston 40 is forced toward the upper limits of its travel, leaving a very small chamber 50. Ideally, the chamber 50 is filled with a compressible fluid to enable the piston 40 to reciprocate slightly as the pumping occurs.

Figure 3:
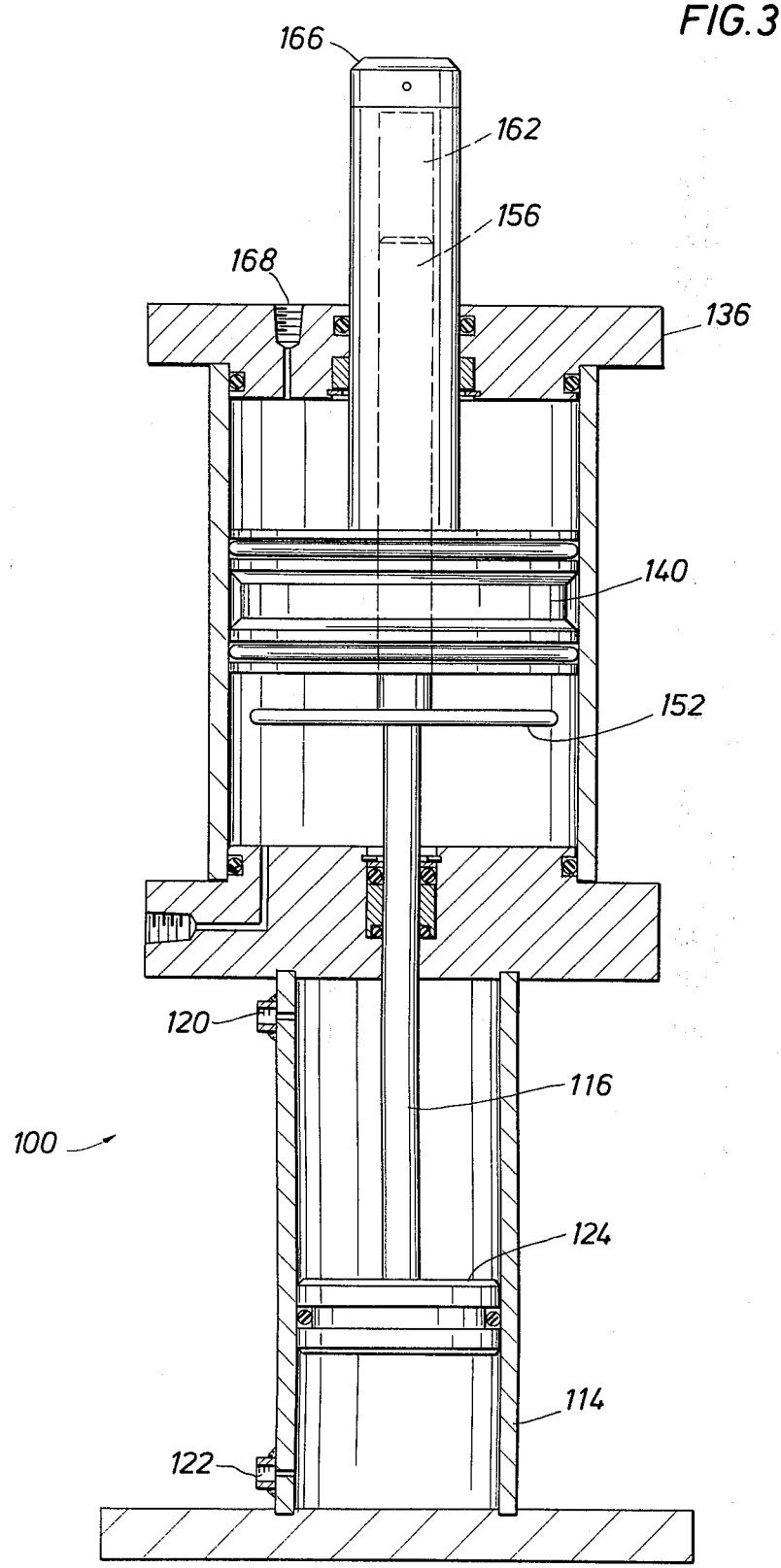
FIG. 3 is a sectional view through an alternate embodiment to the structure of FIG. 1 wherein the structure of FIG. 3 incorporates a double acting hydraulic cylinder in place of the foot powered stirrup.

Attention is next directed to FIG. 3 of the drawings. FIG. 3 shows a structure very similar to the structure of FIG. 1. The differences will be first noted. The similar portions of the apparatus shown in FIGS. 1 and 3 will not be described, and reference is made to the foregoing description. To this end, the structure of FIG. 3 is identified by the numeral 100. The stirring rod 116 is attached to a piston 124 received within a lower cylinder 114. The piston divides the cylinder 114 into upper and lower chambers, and fluid ports are provided at 120 at the top and 122 at the bottom. The two chambers receive hydraulic oil through the ports 120 and 122 under pressure to force the piston 124 upwardly or downwardly. A stirring motion is thus obtained by forcing the piston 124 in reciprocating fashion which in turn transmits movement to the stirring rod 116. The stirrng disc 152 is reciprocated in this fashion. Moreover the disc 152 operates in the same fashion as described for the disc 52. The piston 124 provides an alternate source of power to the foot operated stirrup shown in FIG. 1.

In other regards, the structure shown in FIG. 3 is similar to the structure shown in FIG. 1. To this end, the detailed description of the structure has been abbreviated.

While the foregoing is directed to the preferred embodiment of the present invention, other and further embodiments of the invention may be devised without departing from the basic concept thereof, and the scope thereof is determined by the claims which follow.

I claim:

1. A sample collecting apparatus for collecting and storing a liquid sample wherein the apparatus comprises:
   (a) a cylinder having a head means thereon;
   (b) a piston in said cylinder which defines a sample storage chamber adjacent to said piston in said cylinder;
   (c) inlet means connected to said sample storage chamber and which is adapted to be connected with a source of a sample to deliver a sample to said chamber;
   (d) a stirring plate having a stirring edge in said chamber and which plate is smaller than said chamber to enable said plate to fit within said chamber;
   (e) centered rod means having upper and lower rod portions connected to said stirring plate for positioning said plate in said sample storage chamber which plate extends into sample contained in said chamber to agitate said sample around the stirring edge of said plate on reciprocation of said rod means, said rod means having a length sufficient to extend fully through said sample storage chamber to a location remote from said sample storage chamber;
   (f) foot powered operator means connected to said rod means for forcing said stirring plate to move through said sample storage chamber; and
   (g) said rod means upper portion being larger in diameter than the lower portion thereof with the upper portion thereof being located above said plate and the lower portion being below said plate, and wherein the difference in diameter of said upper and lower portions creates a differential force on admitting a sample to said sample storage chamber under pressure and the differential force urges said plate upwardly in said sample storage chamber toward said piston, and said foot powered operator means forces said plate downwardly overcoming the differential force; wherein said foot powered operator means comprises:
   (1) an upstanding support means for said sample collecting apparatus;
   (2) treadle stirrup means vertically movably received in said support means adjacent to an opening therein;
   (3) connecting means for connecting said stirrup means to said rod means to reciprocate said rod means on movement of said stirrup means;
   (4) said opening formed and sized to enable a user to insert his foot in a reciprocating motion;
   (5) said stirrup means including a foot receiving plate;
   (6) said foot receiving plate and said connecting means being located at the lower end of said lower portion of said rod means;
   (7) roller means connected to said foot receiving plate for guiding said foot receiving plate in reciprocating movement; and
   (8) a surface of said support means contacted by said roller means limiting the reciprocating motion of said foot receiving plate to only vertical motion.

2. The apparatus of claim 1 including a hydraulic fluid receiving chamber above said piston for providing a force acting on said piston to maintain a controlled back pressure on said sample storage chamber through said piston.

3. The apparatus of claim 1 including a hollow piston sleeve connected to said piston and extending upwardly vertically axially of said cylinder and through an upper cylinder head thereof to the exterior of said cylinder and wherein said rod means is axially positioned on the interior of said piston sleeve.

4. The apparatus of claim 1 wherein
   (a) said support means comprises an elongate extension aligned with said cylinder; and
   (b) the opening in said support means comprises an elongate window of sufficient size and length to enable the user to foot power said rod means in reciprocating motion on the interior of said support means.

5. The apparatus of claim 4 wherein said upstanding support means comprises an elongate concentric extension of said cylinder below said head means and which support means is formed of tubular pipe with said opening formed therein.

* * * * *